US010350429B2

(12) United States Patent
Frost

(10) Patent No.: US 10,350,429 B2
(45) Date of Patent: *Jul. 16, 2019

(54) LASER DEVICE FOR INTRACRANIAL ILLUMINATION VIA ORAL OR NASAL FORAMINA ACCESS

(71) Applicant: Ricky A. Frost, Tewksbury, NJ (US)

(72) Inventor: Ricky A. Frost, Tewksbury, NJ (US)

(*) Notice: Subject to any disclaimer, the term of this patent is extended or adjusted under 35 U.S.C. 154(b) by 503 days.

This patent is subject to a terminal disclaimer.

(21) Appl. No.: 14/757,032

(22) Filed: Feb. 8, 2016

(65) Prior Publication Data

US 2017/0225011 A1    Aug. 10, 2017

(51) Int. Cl.
*A61N 5/06* (2006.01)
*A61N 5/067* (2006.01)

(52) U.S. Cl.
CPC ........... *A61N 5/0603* (2013.01); *A61N 5/062* (2013.01); *A61N 5/0618* (2013.01); *A61N 2005/063* (2013.01); *A61N 2005/0606* (2013.01); *A61N 2005/0607* (2013.01); *A61N 2005/067* (2013.01); *A61N 2005/0651* (2013.01); *A61N 2005/0654* (2013.01); *A61N 2005/0659* (2013.01); *A61N 2005/0663* (2013.01)

(58) Field of Classification Search
CPC combination set(s) only.
See application file for complete search history.

(56) References Cited

U.S. PATENT DOCUMENTS

| | | | | |
|---|---|---|---|---|
| 5,640,978 A * | 6/1997 | Wong | A61N 5/0619 | 128/898 |
| 6,450,170 B1 * | 9/2002 | Friedman | A61N 5/0603 | 128/898 |
| 6,471,716 B1 * | 10/2002 | Pecukonis | A61N 5/0616 | 606/11 |
| 6,526,318 B1 * | 2/2003 | Ansarinia | A61N 1/3605 | 607/46 |
| 6,591,049 B2 * | 7/2003 | Williams | G02B 6/0008 | 385/123 |
| 6,918,922 B2 * | 7/2005 | Oron | A61N 5/0613 | 128/898 |
| 7,070,611 B2 * | 7/2006 | Biel | A61N 5/0601 | 128/872 |
| 7,118,563 B2 * | 10/2006 | Weckwerth | A61B 18/203 | 606/9 |
| 7,351,253 B2 * | 4/2008 | DiMauro | A61N 5/0603 | 128/898 |
| 7,544,204 B2 * | 6/2009 | Krespi | A61N 5/0603 | 128/898 |
| 9,180,308 B1 * | 11/2015 | Frost | A61N 5/0622 | |

(Continued)

*Primary Examiner* — Niketa I Patel
*Assistant Examiner* — Shirley X Jian
(74) *Attorney, Agent, or Firm* — Matthew J. Hodulik

(57) ABSTRACT

A system and method of illuminating tissue, particularly within the cranial cavity, through the mouth or nose. The system includes a light source and a power source for powering the light source. Optics are included for directing light from the light source towards the cranial cavity when the apparatus is inserted into a cavity of the head. Light from the light source and output from the optic provides cellular interaction treatment toward a specified area of the head region. Providing illumination where there are already holes in the skull results in more efficient coupling of light to the cells.

20 Claims, 3 Drawing Sheets

(56) References Cited

U.S. PATENT DOCUMENTS

| | | | |
|---|---|---|---|
| 2004/0073278 A1* | 4/2004 | Pachys | A61N 5/0601 607/88 |
| 2005/0107853 A1* | 5/2005 | Krespi | A61B 18/18 607/89 |
| 2005/0240147 A1* | 10/2005 | Makower | A61B 17/24 604/96.01 |
| 2006/0100675 A1* | 5/2006 | Gardner | A61N 5/0621 607/88 |
| 2006/0100679 A1* | 5/2006 | DiMauro | A61N 5/0601 607/94 |
| 2006/0155348 A1* | 7/2006 | deCharms | A61N 5/0601 607/89 |
| 2006/0271024 A1* | 11/2006 | Gertner | A61N 5/0603 606/2 |
| 2006/0287695 A1* | 12/2006 | DiMauro | A61N 5/0603 607/88 |
| 2012/0245659 A1* | 9/2012 | Matthews | A61N 5/0601 607/89 |
| 2013/0138182 A1* | 5/2013 | Nissila | A61N 5/0618 607/88 |
| 2014/0358199 A1* | 12/2014 | Lim | A61N 5/0603 607/92 |
| 2018/0015301 A1* | 1/2018 | Lim | A61N 5/0622 |

* cited by examiner

INFERIOR SKULL

LASER DEVICE FOR INTRACRANIAL ILLUMINATION VIA ORAL OR NASAL FORAMINA ACCESS

RELATED APPLICATIONS

This application is divisional application and claims the benefit of the filing date under 37 CFR 178 of U.S. patent application Ser. No. 12/009,405, entitled LASER DEVICE FOR INTRACRANIAL ILLUMINATION VIA ORAL OR NASAL FORAMINA ACCESS filed Jan. 18, 2008, now U.S. Pat. No. 9,180,308.

TECHNICAL FIELD

This invention relates generally to laser illumination devices and more particularly to laser devices used in medical treatments.

BACKGROUND OF THE INVENTION

Photobiomodulation is a new field of medicine where generally low power light or low power laser radiation is applied to tissue with the idea of prompting a cellular response. Although the physical chemistry is not well understood, some theories and empirical data indicate that the light interacts with the cell mitochondria and stimulates the energy production of the cell. Once cells performing a certain function get energized a physiological response is observed. There are many tens of indications that have been the basis of photobiomodulation experimentation and clinical studies ranging from local aesthesia to dermatological disorders. Some of the areas that have been best studied are increase of blood flow, reduction in inflammation and wound healing. It is known that certain light applied to the skin will cause an increase in blood flow.

An ischemic stroke is caused by a blood clot in the brain limiting blood flow thereto and causing oxygen deprivation. Brain cells die in a stroke, therefore, immediate treatment is necessary to avoid or limit permanent brain damage.

Studies are under way to use lasers to stimulate blood flow to the brain during a stroke. These studies involve illuminating the scalp with a high power laser and shining light through the hair, skin, hair follicles, and skull into the brain.

SUMMARY OF THE INVENTION

An advance is made over the prior art in accordance with the principles of the present invention that is directed to a new approach for a system and method of illuminating tissue, particularly within the cranial cavity, through the mouth or nose. There are previous ideas for attempting to provide illumination on the outside of the skull. Providing laser illumination in areas where there are already holes in the skull results in more efficient coupling of light to the cells. Illuminating the intracranial cavity results in an increase in circulation, increase in lymphatic system, reduction in inflammation, and stimulation of cellular activity. The invention will be used for treatment of headaches, to lessen the effects of stroke if treated during a stroke, and acute trauma.

One embodiment of the invention sets forth an apparatus for illuminating the cranial cavity of a head. The apparatus comprises a light source and a power source for powering the light source. Optics are included for directing light from the light source towards the cranial cavity when the apparatus is inserted into a cavity of the head. Light from the light source and output from the optic provides cellular interaction or photobiomodulation treatment toward a specified area of the head region.

BRIEF DESCRIPTION OF THE DRAWING

The teachings of the present invention can be readily understood by considering the following detailed description in conjunction with the accompanying drawings, in which.

DETAILED DESCRIPTION

Figure 1:
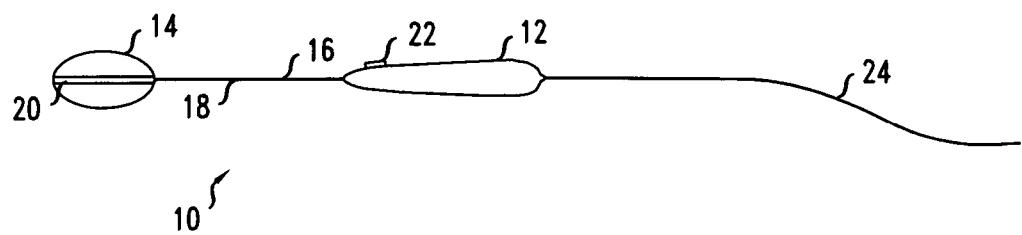
FIG. 1 shows one exemplary embodiment of a laser illumination device in accordance with one aspect of the present invention.

Exemplary embodiments of the invention will now be described while referring to the figures, several of which may be simultaneously referred to during the course of the following description.

Ischemic stroke is a traumatic but common event that afflicts over a half million people each year in the United States alone. A stroke occurs when the blood supply to the brain has been blocked. This most commonly occurs when a clot finds its way to the brain. In most strokes, little harm occurs to the patient at the exact time that the first symptoms appear. Within hours of the first symptoms, however, which in some cases are not even severe enough to warrant a 911 call or a trip to the hospital, permanent damage can occur.

Given the narrow therapeutic window before the effects of stroke can become more severe, timely diagnosis and treatment of ischemic stroke are paramount. Currently, anticoagulants and other drugs are the most well known and effective method used to treat strokes. Early application of photobiomodulation treatment for stroke and other ailments as discussed herein will not replace drugs, but may substantially open the therapeutic window to allow for effective treatment with the drugs.

According to the American Stroke association, the chain of survival for stroke is as follows:
  Detection—Recognition of stroke signs and symptoms;
  Dispatch—Call 9-1-1 and priority EMS dispatch;
  Delivery—Prompt transport and prehospital notification to hospital;
  Door—Immediate ED triage;
  Data—ED evaluation, prompt laboratory studies, and CT imaging;

Decision—Diagnosis and decision about appropriate therapy; and

Drug—Administration of appropriate drugs or other interventions.

The photobiomodulation treatment described herein would ideally be administered at the first sign of stroke symptoms by EMS or directly administered by the patient or another person. Due to the importance of timely treatment for stroke patients and the fact that there are no known side effects to the presently described photobiomodulation treatment, administering treatment in the field before or during patient transportation to the medical facility would appear to be a prudent approach.

As discussed, ischemic stroke occurs when blood supply leading to the brain is blocked by a blood clot. Brain cells that are not able to get enough blood and oxygen die, which may result in a disabling injury or death. The present invention discloses a system and method for illuminating tissue, particularly within the cranial cavity, that may provide an increase in circulation and stimulation of cellular activity to aid in the treatment for stroke. As described herein, the illumination treatment of the present invention takes place through the mouth or nose. Prior art techniques for illuminating the brain apply an illumination source through the outside of the skull. Such techniques may be hampered, however, because the skull, skin and hair absorb, reflect and scatter light. As will be described, providing laser illumination in areas where there are already voids in the skull results in a more efficient coupling of light to the cells that need to be treated.

Photobiomodulation applications have taken place in the prior art using low power light or laser radiation. The power levels required for such applications to have an effect on the tissue can be quite low. There is evidence that suggests power levels from 5 mW to 20 W can be effective for various cellular interactions.

Diode lasers are tiny lasers that efficiently convert electrical energy to electromagnetic radiation. Semiconductor lasers (diode lasers) are typically made from epitaxial layers of AlGaAs or aluminum-free materials grown on a GaAs substrate. The materials are then processed and packaged such that excess heat can be efficiently removed. Given the current state of diode laser technology, single emitter 100-200 micron wide and 1-2 mm long near infrared diode lasers are commercially available with power levels up to about 5 W. Thus, the power levels of laser diodes are within the effective range for use in photobiomodulation treatments. If necessary, multiple single emitters can be coupled on a bar or as single chips in order to provide additional power.

The present invention relates to a system and method for applying radiation from a semiconductor diode laser or other light source to an area below the skull that is accessed via the nasal cavity or mouth. In one embodiment of the invention, light from the light source is transmitted via a fiber optic or light coupler to below the skull and into an area of the brain. In this way, the light source may be located remote from the light output, if desired. Examples of other light sources that may also be utilized in connection with the invention include lamps, flashbulbs and LEDs.

Referring to FIG. 1, one exemplary embodiment of an internal laser illumination device 10 in accordance with the present invention is shown. As shown, the illumination device 10 includes two main portions: a main housing 12 which includes the laser diode, heat sink and power source among other things and a guide plate 14 which is insertable into the mouth and includes the laser output and any suitable optics. The main housing 12 and guide plate 14 are coupled to one another via a rigid or semi-rigid longitudinal member 16 that includes a fiber optic cable 18, e.g., a multi-mode fiber optic cable, positioned therein. Thus, one embodiment of the device resembles a tongue depressor instrument or even a lollipop that is graspable by way of the housing section. Although the guide plate 14 is shown as having an essentially flat shape, it would be understood that this portion of the device may take on a variety of different shapes, e.g., semi-spherical and other shapes having one flat side, that would also be suitable for photobiomodulation applications. The fiber optic cable 18 enables the laser output 20 from the laser diode to be directed to and output from the guide plate in a desired manner. Also by coupling the main housing and guide plate together by way of a semi-rigid even flexible member 16, a patient or caregiver using the device will be able to hold and manipulate the device in a manner comfortable to the patient.

In one embodiment of the invention, the laser source is configured like a conventional laser pointer. That is, a power source and laser diode may be located in the housing 12 having an activation mechanism 22, such as a switch or turn activator, which when placed in the activation position energizes the laser diode via the power source. In the shown embodiment, the power source is a battery. Assuming a 5 W laser diode, a 1.5V, 7 A battery would be suitable for use as a power source for use with the present invention. Batteries with sufficient current capability for operation of the above-type laser diodes over a one half hour time period, for example, are commercially available. A person skilled in the art would realize that different size batteries may be utilized depending on the power requirements of the diode and the specific operating parameters. Providing power to the device of the present invention via battery enables the device to be portable, so that the device may be easily transported with an individual during use. It would be understood, however, that the device of the present invention may alternatively be AC powered via cord 24 and conventional wall outlet, or may be operable in conjunction with a rechargeable battery, so that the device may be chargeable for later operation over a given period of time. In the case of a rechargeable unit, the illumination device of the present invention would be insertable into a separate charging base for charging purposes or else be adapted to accept the input of a charging unit in a fashion similar to that of a cell phone charger. One example of a suitable design for rechargeable equipment incorporating laser diodes is given in U.S. Pat. No. 7,118,563 to Weckwerth et al., the contents of which are incorporated by reference herein.

Figure 2:
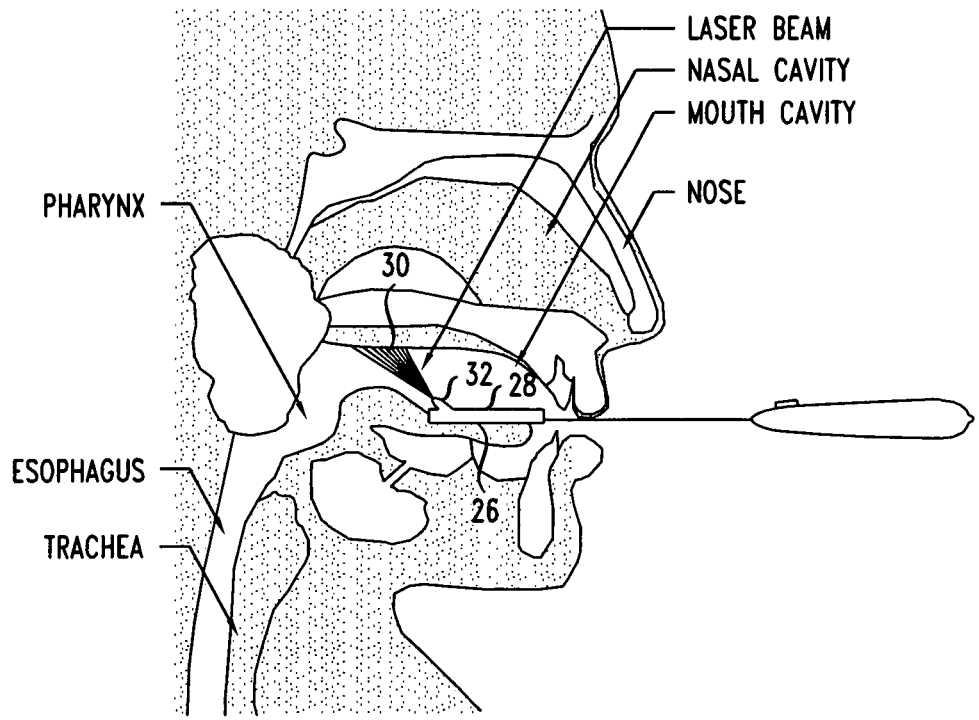
FIG. 2 shows one embodiment of a laser illumination device as used in connection with the methodology of the present invention.

In the shown embodiment of the device, the guide plate 14 which is insertable into the mouth, and which includes the laser output 20 part of the device, is flat on one side 26 and the laser output of the device is included on an opposite side 28 (see FIG. 2). The laser output side of the device, when inserted into the oral cavity and turned on, directs the output laser light 30 upwards in a general direction towards the roof of the mouth. Instructions on the device indicate the direction of orientation for the laser output, for example, one side of device may have indicia thereon, at the guide plate, for example, indicating "this side up" and/or "this side on tongue". The device also includes an optical device such as a lens 32 that couples to the end of the fiber optic cable and generally serves to direct or scatter the light source and generate a desired spot size at a specific location, for example at the back of the mouth. The optical component also serves to encapsulate and offer protection to the tip of the fiber optic. In the case of institutional models of the present invention that will be reused, the guideplate will be adapted to accept a disposable encapsulant, e.g., a transparent cover, to enable easy re-use. In either case, appropriate portions of the device will be sealed in order to protect the device from moisture or other contaminants and so that a re-usable device may be efficiently cleaned.

Figure 3:
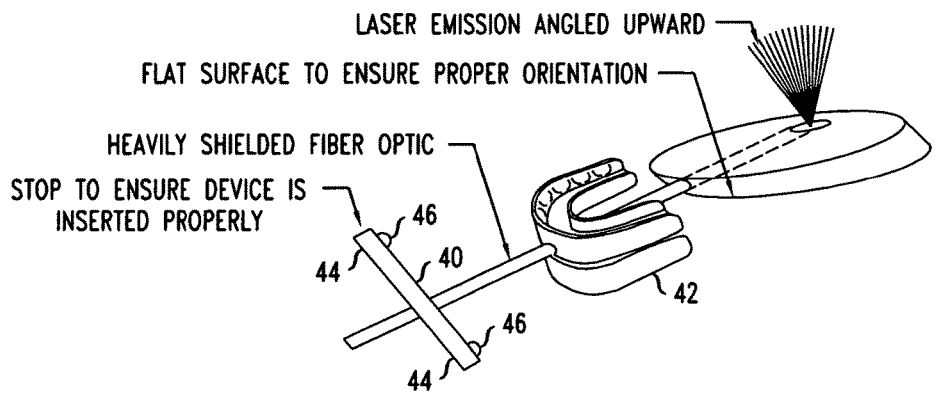
FIG. 3 shows another exemplary embodiment of a laser illumination device in accordance with the present invention.

Referring to FIG. 3, the device would also have a guard or stop 40 to show generally how far to insert the device into one's mouth. As shown, the stop 40 is illustrated as a transverse cross member that is attached at a location along the longitudinal member. Since the stop has wider dimensions than a person's mouth, once the stop is in contact with the outer portion of a patient's mouth, this will be an indication that the device should not be inserted any farther into the mouth. At the same time, when the stop member of the device is positioned at or near the outside of the patient's mouth, this will indicate favorable placement of the device in order to direct radiation toward the roof an individual's mouth. It would be understood, that the stop 40 may take on various different forms as long as the stop acts to assist with proper placement in the oral cavity. For instance, the stop could be a biteplate or mouthpiece that is insertable into a patient's mouth. In addition, the stop could be made to be adjustable depending on the internal size of a patient's mouth such that optimal orientation within the mouth is always achieved. For example, the adjustable insertion depth may be gauged by the head size or other related metric of a patient or may be based on the general feel within the mouth—e.g., so as not to initiate a gag reflex. In order to make the stop adjustable, the longitudinal member may have a number of preset positions into which the stop may be set in place thereon, such that the stop is able to be moved along the longitudinal member and be clamped or affixed into at one of the preset positions. Other known methods for maneuvering and holding the stop in place along the longitudinal member may also be utilized.

Still referring to FIG. 3, in one exemplary embodiment of the invention, the device of the present invention may also be equipped with a safety interlock to ensure that appropriate portions of the device are completely inside the mouth before the laser can be turned on. A safety interlock feature in accordance with the present invention can be achieved in a variety of manners, as will be described. In one embodiment, a biteplate 70 having a mechanical switch within is provided. A user of the laser illumination device is required to bite down on one or more areas of the biteplate 42 into which dental contact would take place in order to activate (or close) the included switch. Once the switch is activated, indicating that the laser is encompassed within the user's mouth, the laser is enabled.

In another embodiment, the safety interlock is an ohmic interlock 44. Here, a benign voltage is applied to one of two electrodes 46 on the device. The electrodes 46 can be placed, for example, on the bottom 26 of the (lollipop) guide plate 14 or on a part of the device that is outside of the mouth, such as the stop, where portions of the stop may be curved in order to make wrap around contact with a user's face. When both of the electrodes are in contact with a surface of the skin or mouth, an electrical circuit is completed, since resistance of the body is within a certain known range. The completed circuit enables the laser to be safely tuned on within the patient's mouth.

In another embodiment, a photonic sensor may be utilized, such that if light was present at wavelengths shorter than 600 nm, for example, visible light ranges, then the laser would not turn on. Accordingly, if the patient's mouth was open or opens, then the laser will in turn deactivate.

Another option is the use of a bio-sensor, which senses the heartbeat of a patient, through contact with the inside of the patient's mouth, for example, in order for the laser to be activateable. One or more of the above described safety interlocks may be utilized in order to ensure safe operation of the present invention laser illumination device. An LED or other visual indicator may also be included on the outside of the device such that the patient or any attending medical professional can readily determine that the laser light source is in operation. An audible indicator may also be utilized instead of or in addition to the visual indicator to demonstrate operation.

Referring to FIG. 2, there is shown a depiction of the illumination device 10 as it is inserted into the oral cavity of a patient. As can be seen, light or radiation 30 from the device is directed upwards toward the roof of one's mouth when the device is energized. Since there are a number of voids within the bone structure on the inside of the human head, as the light is directed upwards an efficient coupling of light or laser radiation is able to be achieved into the brain area. More specifically, other known methods of applying laser radiation through the outside of the skull encounter difficulties in penetrating the skull as well as reflections from the hair and skin. Since the ability to provide quick and meaningful treatment to a stroke victim can mean the difference between lasting injuries and less severe complications, having a mechanism for the easy and effective delivery of laser light for photobiomodulation may offer significant advantages for this type of treatment.

As discussed above, a fiber pigtailed laser diode, although not necessary, is a viable approach to illuminate the cranium through the foramina. The fiber pigtailed approach offers a few advantages. Firstly, it separates the electrical supply from the tissue. This would not be entirely necessary as the voltage will be relatively low on the diode anyway, however, there may be some safety and regulatory issues that make the approach particularly advantageous. Moreover, if it is later determined that there is more of a clinical advantage to input the light through the nasal cavity, then the fiber optic probe will offer a significant advantage due to the relatively small diameter and flexibility of the fiber optic cable. Also, depending upon the power of the diode, it may be quite awkward to insert a diode and heat sink into either the nose or mouth. With respect to nasal insertion, this would also mandate that the diode laser be on the lower end of the power range discussed, since the power density at the output of the fiber will be much higher than if the laser is allowed to diverge to a nominal one inch spot, for instance, on the roof of the mouth, as in the case of oral insertion. From a very general standpoint, except for the reasons mentioned above relating to the fiber coupling, there is no therapeutic need for high brightness.

Figure 4:
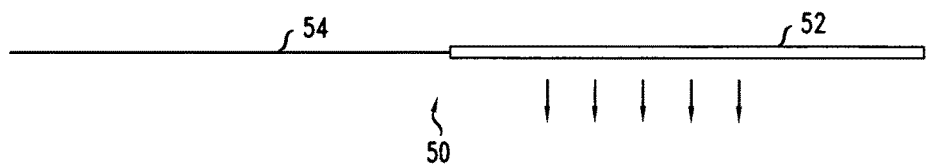
FIG. 4 shows an exemplary embodiment of a laser illumination device suitable forinsertion into the nasal cavity.

Referring to FIG. 4, there is shown another exemplary embodiment of a laser illumination device 50 in accordance with the present invention. The shown embodiment is especially adapted for insertion into the nasal cavity. The basic structure of the device is similar to the device used for insertion into the mouth except that the guide plate 52 is adapted for insertion into the nose as opposed to the mouth. In the shown embodiment, the guide plate 52 is or is adapted for use with a side-firing fiber 54. The side-firing fiber 54 differs from a conventional fiber optic in that rather than light being transmitted out of the end of the fiber, the light is output from the sides of the fiber, where the output may be made to be up to 360 degrees around or any interval or intervals less than 360 degrees. Here, the guide plate, which may be some form of encapsulant, is generally cylindrical in shape and serves to orient the output of the fiber optic in a rearward and upward direction toward the brain as opposed to the more upward orientation of the mouth insertable version. Other mechanisms for outputting and orienting light transmitted from a conventional or side-firing laser may also be utilized.

Figure 5:
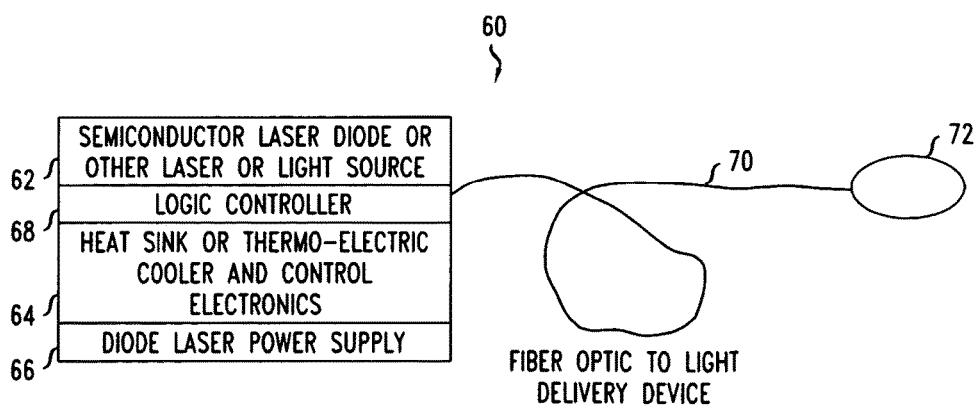
FIG. 5 shows a block diagram of a laser illumination device in accordance with the principles of the present invention.

Referring to FIG. 5, there is shown a block diagram of one embodiment of a laser illumination device 60 in accordance with the present invention. As shown, the main housing of the device includes a laser diode 62 and heatsink 64. A power source 66, either a battery or AC power source, as discussed, powers the laser diode and is activated by a switch. The laser diode is controlled by a logic controller 68 which controls the output of the laser diode to be either continuous or to produce pulses of a specific duration, as would be understood. As mentioned, the logic controller will also be capable of producing a pulsed output, where a pulsed output is recognized as being a preferable delivery mechanism for stimulation of cells for certain treatments. Lasers are commercially available that deliver 7 W of average power, for example, Biolase model ezlase (http://www.biolase.com/ezlase/) is a commercial laser delivering 7 W of average power at 810, 940, 980 nm. A fiber optic 70 similar to that of the Ezlase™ couples to the output of the laser. A mechanical housing 72 for the fiber, shaped as described herein, for example, like a lollipop, for orienting the fiber appropriately on the tongue couples to or includes parts of the fiber optic 70 therein. An optic (or lens) is coupled after the fiber in the disc part (guide plate) of the lollipop to project the light in the appropriate direction and to the appropriate spot size on the back of the roof of the mouth. In one exemplary embodiment of the invention a spot size of approximately one inch or greater in diameter is projected onto the roof a mouth. The spot size would be variable based on lens type and depending on the intended application of the treatment. In addition, the wavelength of the laser would be in the range of 500-1100 nm, as lasers with wavelengths between 630-1000 nm have good tissue transmission, thus, those wavelengths are considered to be generally acceptable for the instant application.

Figure 6:
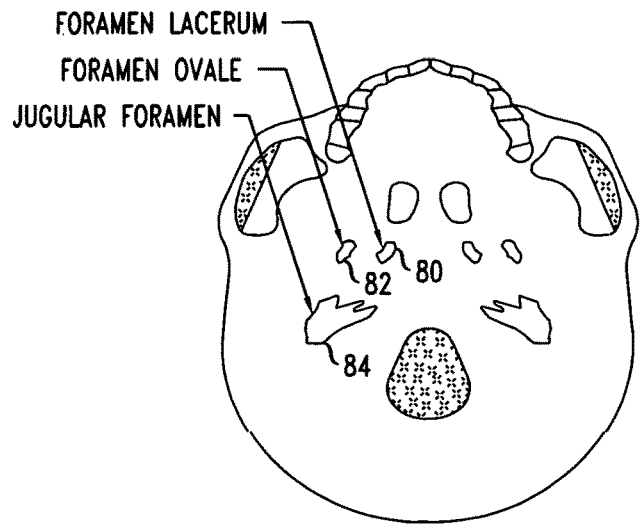
FIG. 6 shows a bi-lobal energy distribution from the output of laser illuminationdevice in accordance with one aspect of the present invention.
Figure 7:
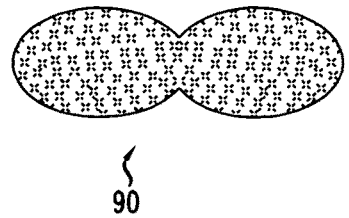
FIG. 7 is a cross-section of the skull illustrating various foramina.
Figure 8:
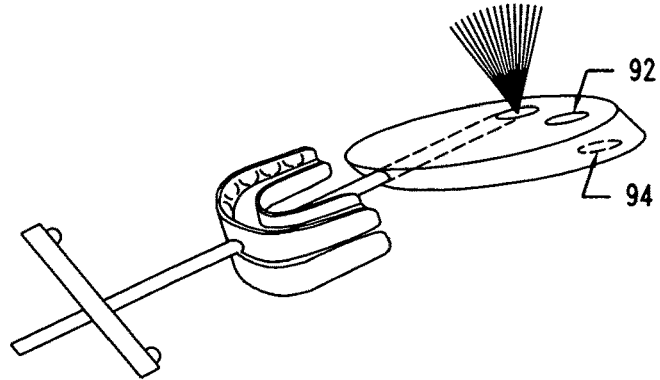
FIG. 8 shows another exemplary embodiment of a laser illumination device in accordance with the present invention.

The laser spot could be a round, oval, bi-lobal, or other shaped image on the back of the roof of the mouth. Referring to FIG. 6 in combination with FIG. 2, it can be seen that in the center of the back of the mouth, the bottom of the skull will block radiation from entering the cranium. FIG. 6 shows a high level top cross-section of the human inferior skull which illustrates the locations of the various foramina 80, 82, 84 of the skull. It may be advantageous to have the energy distribution that is delivered to the roof of the mount be bi-lobal, multi-lobal or otherwise patterned to thereby better overlap with the foramina of the skull. See FIG. 7 which illustrates a bi-lobal energy distribution 90 which may be achieved with a dual or split fiber output or similar functioning lens. With this approach the light to the brain may be optimized without excessive heating to the mouth.

As discussed, the present invention may be used to deliver photobiomodulation treatment for a number of different indications including, but not limited to: acute aschemic stroke, memory improvement, improving the thought process, treatment for diseases of the brain, acute trauma to the head, excitation of glands in the head, photodynamic therapy, etc. Illuminating the intracranial cavity results in an increase in circulation, increase in lymphatic system, reduction in inflammation, and stimulation of cellular activity. Accordingly, the invention may be used for treatment of headaches, to lessen the effects of stroke if treated during a stroke, and acute trauma.

The intracranial illumination device of the present invention can be put into operation once it is determined that a condition exists that could benefit from photobiomodulation treatment to the head or brain area, for example, any of the indications described above, such as aschemic stroke, head trauma, etc. Operation of the device is relatively simple, where the device is turned on and inserted into the oral or nasal cavity to a prescribed depth. The appropriate depth may be indicated by contact with the stop of the device at the exterior of a patient's oral or nasal cavity. Or the appropriate depth of insertion may be obtained by feel within the patient's mouth or nose—(where general discomfort would indicate over-insertion). The device can remain on and in application mode for a prescribed period of time. As described previously, a safety interlock feature may also be included in the device, wherein appropriate measures would need to be taken by the user or care giver before the illumination device will activate. The inventor is unaware, however, of any potential side effects for treatment of tens of minutes at power levels of single digit wattage using the present invention.

The foregoing description merely illustrates the principles of the invention. It will thus be appreciated that those skilled in the art will be able to devise various arrangements, which, although not explicitly described or shown herein, embody the principles of the invention, and are included within its spirit and scope. Furthermore, all examples and conditional language recited are principally intended expressly to be only for instructive purposes to aid the reader in understanding the principles of the invention and the concepts contributed by the inventor to furthering the art, and are to be construed as being without limitation to such specifically recited examples and conditions. Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future, i.e., any elements developed that perform the same function, regardless of structure. Many other modifications and applications of the principles of the invention will be apparent to those skilled in the art and are contemplated by the teachings herein. Accordingly, the scope of the invention is limited only by the claims.

What is claimed is:

1. A method for illuminating the cranial cavity of a head, said method comprising:
    inserting a light guide into a cavity of the head being the oral cavity, said light guide providing light from a light source in a range of between 500-1100 nm; and
    directing light from said light source towards said cranial cavity, wherein light from said light source and output from said light guide provides photobiomodulation treatment toward a specified area of the head region
    further including optics for directing light from said laser light source and providing a light beam with a light pattern having a spot size and spot shape toward the back of said oral cavity, said light beam aligning with at least the lacerium foramina of the skull and providing light through said at least lacerium foramina into said cranial cavity said light source configured to provide light of sufficient power level and wavelength in order to penetrate tissue within the head region and reach said cranial cavity through said at least lacerium foramina.

2. The method of claim 1, wherein said light source is selected from the group consisting of laser diode and laser.

3. The method of claim 2, wherein said light source produces an average output power in the range of 150 mW-20 W.

4. The method of claim 1, wherein the light source is a laser diode having an output power level between 150 mW-20 W.

5. The method of claim 1, wherein the light source is operable in connection with a safety interlock mechanism for preventing output of the light source when the apparatus is outside of said cavity.

6. The method of claim 1, wherein the light source is a laser diode.

7. The method of claim 1, wherein the light source is a red or NIR laser from 630-1100 nm.

8. The method of claim 1, wherein light from the light source is used for treatment of indications selected from the group consisting of: stroke, memory improvement, improving the thought process, treatment for diseases of the brain, acute trauma to the head, illumination of glands in the head, photodynamic therapy and stimulation of the lymphatic system.

9. The method of claim 1, wherein optics create a pattern that is directed through foramina of the skull.

10. The method of claim 9, wherein the light guide is for insertion into the oral cavity, wherein optics are adapted to output a multi-lobal energy distribution, wherein at least two output lobes are directed towards oral foramina of the skull.

11. The method of claim 1, further including a guide plate adapted for contact with the tongue for accepting and orienting the light output from said optics toward a given region of the head.

12. The method of claim 11, wherein said guide plate has at least one generally flat planar side.

13. A method for providing photobiomodulation treatment by application of a laser light source to the cranial cavity, said method comprising:
providing a laser light source, a power module for powering said light source and an optical transmission medium coupled to said light source;
inserting a guide plate into a mouth of a human patient, said guideplate coupling with said optical transmission medium, said guide plate having a generally planar bottom surface that rests substantially flat on a tongue of said patient, said guide plate adapted to, when positioned on the tongue, orient a light beam produced from said light source and traveling through said optical transmission medium in a spot size and output pattern that irradiates the roof of the mouth so as to direct and align a portion of said light beam with at least one foramina of the skull, said guide plate further including optics on an opposite side of said generally planar bottom surface for outputting said light beam, light from said light beam being directed through said at least one foramina of the skull such that light from said laser light source penetrates tissue within said mouth to travel in a desired direction within the cranial cavity, said laser light source providing light of sufficient power and wavelength in order to penetrate said tissue within said mouth and enter said cranial cavity of said skull through said at least one foramina to thereby provide said photobiomodulation treatment.

14. The method of claim 13, wherein light from the light source is used for treatment of indications selected from the group consisting of: stroke, memory improvement, improving the thought process, treatment for diseases of the brain, acute trauma to the head, illumination of glands in the head, photodynamic therapy and stimulation of the lymphatic system.

15. The method of claim 13, wherein said light source produces an average output power in the range of 150 mW-20 W.

16. The method of claim 13, wherein said light source produces an average output power in the range of 5 mW-20 W and a given spot size.

17. A method for providing photobiomodulation treatment by application of a laser light source to the cranial cavity, said method comprising:
providing a laser light source, a power module for powering said light source and an optical transmission medium coupled to said light source;
inserting a guide plate into a mouth of a patient, said guideplate coupling with said optical transmission medium, said guide plate acting to orient light produced from said light source and traveling through said optical transmission medium in a desired direction within the cranial cavity when the guide plate is placed into the mouth of said patient;
said guide plate configured for insertion into a mouth of a human patient for coupling with said optical transmission medium, said guide plate having a generally planar bottom surface that rests substantially flat on a tongue of said human patient, said guide plate further including optics on an opposite side of said generally planar bottom surface and a lens configured to orient a light beam produced from said light source and traveling through said optical transmission medium toward the back of said mouth in a spot size and output pattern that irradiates said back of said mouth so as to direct and align said light beam with at least one foramina of the skull, light from said light beam being directed through said at least one foramina of the skull such that light from said laser light source penetrates tissue within said mouth to travel in a direction based on orientation of said lens within the cranial cavity, said laser light source providing light of sufficient power and wavelength in order to penetrate said tissue within said mouth and enter said cranial cavity of said skull through said at least one foramina to thereby provide said photobiomodulation treatment
wherein said lens is configured to output a multi-lobal energy distribution, wherein at least two output lobes are directed through oral foramina of the skull and wherein the light source is a laser diode having a wavelength in the range of 500-1100 nm.

18. The method of claim 17, wherein light from the light source is used for treatment of indications selected from the group consisting of: stroke, memory improvement, improving the thought process, treatment for diseases of the brain, acute trauma to the head, illumination of glands in the head, photodynamic therapy and stimulation of the lymphatic system.

19. The method of claim 17, wherein the light source is operable in connection with a safety interlock mechanism for preventing output of the light source when the apparatus is outside of the mouth.

20. The method of claim 17, wherein said light source produces an average output power in the range of 5 mW-20 W and a given spot size.

* * * * *